(12) United States Patent
Hwang et al.

(10) Patent No.: US 10,388,593 B2
(45) Date of Patent: Aug. 20, 2019

(54) SENSOR

(71) Applicant: LG ELECTRONICS INC., Seoul (KR)

(72) Inventors: Insung Hwang, Seoul (KR); Wonhyeog Jin, Seoul (KR); Moosub Kim, Seoul (KR); Yunguk Jang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 11 days.

(21) Appl. No.: 15/497,661

(22) Filed: Apr. 26, 2017

(65) Prior Publication Data

US 2017/0316995 A1    Nov. 2, 2017

(30) Foreign Application Priority Data

Apr. 27, 2016    (KR) .......................... 10-2016-0051534

(51) Int. Cl.
| | |
|---|---|
| *H01L 23/482* | (2006.01) |
| *G01N 27/12* | (2006.01) |
| *H01L 23/00* | (2006.01) |

(52) U.S. Cl.
CPC ....... *H01L 23/4821* (2013.01); *G01N 27/123* (2013.01); *G01N 27/128* (2013.01); *H01L 24/29* (2013.01); *H01L 24/32* (2013.01); *H01L 24/48* (2013.01); *H01L 24/73* (2013.01); *H01L 2224/293* (2013.01); *H01L 2224/48091* (2013.01); *H01L 2224/48227* (2013.01); *H01L 2224/73265* (2013.01);
(Continued)

(58) Field of Classification Search
CPC . H01L 23/053; H01L 23/4821; G01N 27/125; G01N 27/123; G01N 27/128
See application file for complete search history.

(56) References Cited

U.S. PATENT DOCUMENTS

| | | |
|---|---|---|
| 6,525,413 B1 | 2/2003 | Cloud et al. |
| 2014/0192412 A1* | 7/2014 | Imai .................... G02B 27/0006 359/514 |
| 2015/0198551 A1 | 7/2015 | Jun et al. |

FOREIGN PATENT DOCUMENTS

| | | |
|---|---|---|
| JP | 2002174608 | 6/2002 |
| JP | 2012078089 | 4/2012 |
| JP | 2012098233 | 5/2012 |

OTHER PUBLICATIONS

PCT International Application No. PCT/KR2017/004374, International Search Report dated Aug. 4, 2017, 11 pages.

* cited by examiner

*Primary Examiner* — Wael M Fahmy
*Assistant Examiner* — Sarah K Salerno
(74) *Attorney, Agent, or Firm* — Lee Hong Degerman Kang & Waimey

(57) ABSTRACT

A sensor is disclosed. The sensor comprises a first substrate; a second substrate positioned relative to the first substrate; a first electrode located between the first substrate and the second substrate, the first electrode formed on the second substrate; a sensing portion covering at least a part of the first electrode and further covering at least a portion of the second substrate; a pad electrode located between the first substrate and the second substrate, wherein the pad electrode is formed on the second substrate and is electrically coupled to the first electrode; and a bonding pad located between the first substrate and the second substrate, wherein the bonding pad is formed on the first substrate and is electrically coupled to the pad electrode.

14 Claims, 24 Drawing Sheets

(52) U.S. Cl.
CPC ............... *H01L 2924/00014* (2013.01); *H01L 2924/16151* (2013.01); *H01L 2924/16152* (2013.01)

SENSOR

CROSS-REFERENCE TO RELATED APPLICATIONS

Pursuant to 35 U.S.C. § 119(a), this application claims the benefit of earlier filing date and right of priority to Korean Patent Application No. 10-2016-0051534, filed on Apr. 27, 2016, the contents of which are hereby incorporated by reference herein in their entirety.

BACKGROUND OF THE INVENTION

Field of the Invention

The present invention relates to a sensor. Particularly, the present invention relates to a gas sensor capable of sensing a gas.

Discussion of the Related Art

A sensor may detect its surroundings or changes of the surroundings. A sensor is a kind of transducer in that the sensor can provide various types of signals including electric and optical one.

A gas sensor can detect a certain gaseous material. A gas sensor is important because they detect gas may include toxic material harmful to human or animal.

Recently, with the development of miniaturization technology, such a sensor has been downsized, and the size of the sensor has been reduced from the meter to the micrometer unit in advance. The miniaturization technology of the sensor can be used not only to reduce the size of the sensor but also to maintain the sensitivity of the sensor, the responsiveness of the sensor, the durability of the sensor, and the economical efficiency of the sensor manufacturing.

SUMMARY OF THE INVENTION

Accordingly, one object of the present invention is to address the above-noted and other drawbacks of the related art.

Another object of the present invention is to provide a sensor having improved property of sensitivity.

Another object of the present invention is to provide a sensor having improved durability.

Another object of the present invention is to provide a sensor in which gas can easily enter and exit.

In one aspect, there is provided a sensor comprising a first substrate; a second substrate positioned relative to the first substrate; a first electrode located between the first substrate and the second substrate, the first electrode formed on the second substrate; a sensing portion covering at least a part of the first electrode and further covering at least a portion of the second substrate; a pad electrode located between the first substrate and the second substrate, wherein the pad electrode is formed on the second substrate and is electrically coupled to the first electrode; and a bonding pad located between the first substrate and the second substrate, wherein the bonding pad is formed on the first substrate and is electrically coupled to the pad electrode.

The first substrate may include an opening adjacent to the sensing portion.

The second substrate may include an opening adjacent to the sensing portion.

The first substrate may include a first opening adjacent to the sensing portion, the second substrate may include a second opening adjacent to the sensing portion, and positioning of the first opening relative to the second opening may permit gas exchange in an out of the sensor through the first opening and the second opening.

The second substrate may include: an outer substrate including an hollow space located at a central portion of the outer substrate; an inner substrate located in the hollow space, the inner substrate spaced apart from the outer substrate; and a bridge electrically coupling the outer substrate with the inner substrate.

The pad electrode may be positioned on the outer substrate, the first electrode may be positioned on the inner substrate, and the first electrode may be electrically coupled with the pad electrode via the bridge.

The bonding pad may include a guide, and the guide may face a side surface of the second substrate.

The sensor may further comprise a filter coupled to the first substrate, the first substrate may include an opening formed adjacent to the sensing portion, and the filter may be located to cover the opening.

The sensor may further comprise a filter coupled to the second substrate, the second substrate may include an opening formed adjacent to the sensing portion, and the filter may be located to cover the opening.

The first electrode may include: a heating electrode electrically insulated from the sensing portion; and a sensing electrode electrically coupled to the sensing portion.

The sensing electrode may be positioned in a layer. The heating electrode may be positioned in another layer.

The sensing electrode may be positioned in a layer in which the heating electrode is positioned.

The sensor may further comprise an electrode line formed on the first substrate. The electrode line may be electrically coupled to the bonding pad.

The bonding pad forms a stepped portion. A corner of the second substrate may be positioned adjacent to the stepped portion.

The sensing portion may include a metal oxide.

The sensing portion may be formed on the second substrate.

The first substrate may include an opening that is located to cooperate with the sensing portion.

The first substrate may include an opening that is aligned relative to the sensing portion.

A top side of the second substrate may face a bottom side of the first substrate.

According to at least one of embodiments of the present invention, property of the sensor regarding sensitivity may be improved.

According to at least one of embodiments of the present invention, durability of the sensor may be improved.

According to at least one of embodiments of the present invention, gas can easily enter and exit in the sensor.

Further scope of applicability of the present invention will become apparent from the following detailed description. It should be understood, however, that the detailed description and specific examples, such as the preferred embodiment of the invention, are given by way of illustration only, since various changes and modifications within the spirit and scope of the invention will become apparent to those skilled in the art.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE EMBODIMENTS

Figure 1:
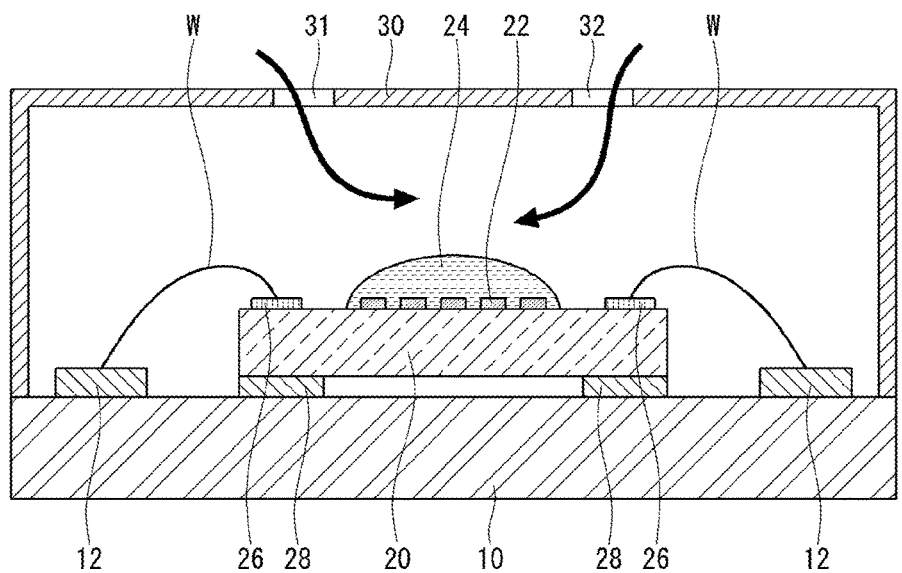
FIG. 1 is a view showing an example of a gas sensor package according to the present invention.

Reference will now be made in detail embodiments of the invention examples of which are illustrated in the accompanying drawings. Since the present invention may be modified in various ways and may have various forms, specific embodiments are illustrated in the drawings and are described in detail in the present specification. However, it should be understood that the present invention are not limited to specific disclosed embodiments, but include all modifications, equivalents and substitutes included within the spirit and technical scope of the present invention.

The terms 'first', 'second', etc. may be used to describe various components, but the components are not limited by such terms. The terms are used only for the purpose of distinguishing one component from other components. For example, a first component may be designated as a second component without departing from the scope of the present invention. In the same manner, the second component may be designated as the first component.

The term "and/or" encompasses both combinations of the plurality of related items disclosed and any item from among the plurality of related items disclosed.

When an arbitrary component is described as "being connected to" or "being linked to" another component, this should be understood to mean that still another component (s) may exist between them, although the arbitrary component may be directly connected to, or linked to, the second component. In contrast, when an arbitrary component is described as "being directly connected to" or "being directly linked to" another component, this should be understood to mean that no component exists between them.

The terms used in the present application are used to describe only specific embodiments or examples, and are not intended to limit the present invention. A singular expression can include a plural expression as long as it does not have an apparently different meaning in context.

In the present application, the terms "include" and "have" should be understood to be intended to designate that illustrated features, numbers, steps, operations, components, parts or combinations thereof exist and not to preclude the existence of one or more different features, numbers, steps, operations, components, parts or combinations thereof, or the possibility of the addition thereof.

Unless otherwise specified, all of the terms which are used herein, including the technical or scientific terms, have the same meanings as those that are generally understood by a person having ordinary knowledge in the art to which the present invention pertains. The terms defined in a generally used dictionary must be understood to have meanings identical to those used in the context of a related art, and are not to be construed to have ideal or excessively formal meanings unless they are obviously specified in the present application.

The following exemplary embodiments of the present invention are provided to those skilled in the art in order to describe the present invention more completely. Accordingly, shapes and sizes of elements shown in the drawings may be exaggerated for clarity.

Gas sensors can be classified into solid electrolyte type, contact combustion type, electrochemical type, and semiconductor type sensor. The semiconductor type gas sensor may be referred to as a semiconductor type micro gas sensor. The semiconductor type gas sensor can detect the presence or absence of a specific gas having a certain concentration or more by measuring the change in the electrical conductivity of the sensing material when the specific gas is adsorbed to the sensing material of the sensor.

Hereinafter, a semiconductor type gas sensor will be described as an example. However, it is not that the above-mentioned types of gas sensors except the semiconductor type gas sensor are excluded.

The gas sensor can detect carbon monoxide (CO), methane ($CH_4$), ethanol ($CH_2H_6O$), and the like. The types of gases that can be detected or sensed by the gas sensor vary widely and are not limited to the gases mentioned above.

In other words, the gas sensor can detect or sense a harmless or beneficial gas to the human body as well as a gas harmful to the human body. For example, a gas sensor can sense the air quality of a given surroundings, which means that the quality of the air can be determined by beneficial gases such as oxygen as well as harmful gases.

FIG. 1 is a view showing an example of a gas sensor package according to the present invention.

The electrode lines 12 may be formed on the first substrate 10. The electrode line 12 may be a plurality of electrode lines 12. The second substrate 20 may be fixed on the first substrate 10. The second substrate 20 may be bonded onto the first substrate 10. The second substrate 20 may be fixed on the first substrate 10 with a metal paste 28.

The electrode 22 may be formed on the second substrate 20. The electrode 22 may be a heating electrode or a sensing electrode. The detecting portion 24 may be formed on the electrode 22. The detecting portion 24 may sense the presence or absence of a gas. For example, the detecting portion 24 may include a metal oxide. The metal oxide may be $SnO_2$. The detecting portion 24 may change conductivity when gas molecules are contacted on the detecting portion 24.

The pad electrode 26 may be formed on the second substrate 20. The pad electrode 26 may be spaced apart from the detecting portion 24 and the electrode 22. The pad electrode 26 may be electrically connected to the electrode 22. The pad electrode 26 and the electrode line 12 may be connected electrically by a wire W.

The housing 30 may be coupled to the first substrate 10. The housing 30 may form a cavity above the detecting portion 24. The housing 30 may have opening 31 and 32. The opening 31 and 32 may be a plurality of openings 31 and 32.

Thus, the gas entered in the housing 30 through the openings 31 and 32 can be brought into contact with or bonded to the detecting portion 24. The conductivity of the detecting portion 24 may be changed if a foreign substance such as a gas contacts or adheres to the detecting portion 24. For this reaction, the heating electrode among the electrode 22 may provide heat to the sensing portion 24. The change of the conductivity causes a change in resistance between sensing electrodes which belong to the electrode 22. The presence or absence of the gas can be confirmed electrically.

However the gas sensor package may have poor coupling between the detecting portion 24 and the electrode 22 or the second substrate 20. When the pad electrode 26 and the electrode line 12 are coupled to each other via the wire W, the detecting portion 24 may be separated or peeled off due to a physical or thermal impact.

In addition, diffusion of the gas may be restricted by the housing 30 provided for protecting the detecting portion 24 and the like, which may degrade the gas sensitivity of the gas sensor. For example, there may be a problem in that the sensing reaction may be continued because the gas that has been once introduced does not escape to the outside and stays there for a long time.

FIGS. 2 to 5 illustrate examples of electrodes according to an embodiment of the present invention.

Figure 2:
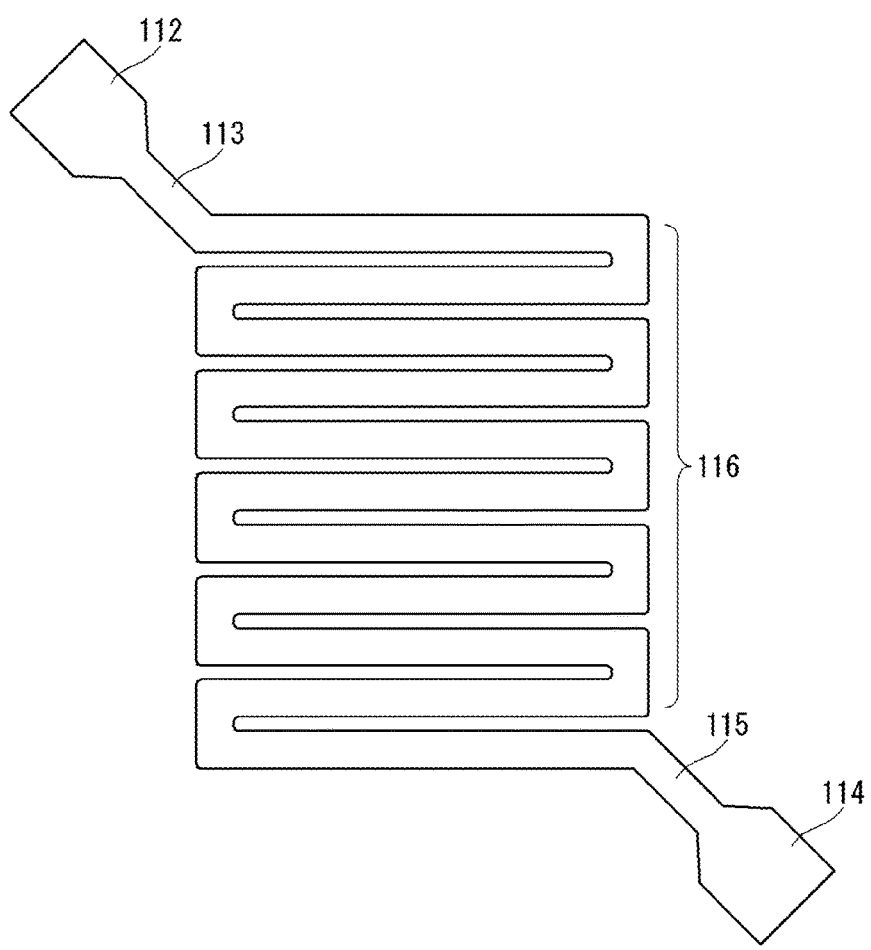
FIGS. 2 to 5 are views showing examples of electrodes according to an embodiment of the present invention.

Referring to FIG. 2, the electrode 110 may be a heating electrode 110. The electrode 110 may be referred to as a first electrode 110. The heating electrode 110 may include a heating portion 116, and connection portions 113 and 115. The heating portion 116 may be formed of a metal having a resistance. For example, the resistance of the heating portion 116 may be 100 ohms. The heating portion 116 can be wound. The heating portion 116 can be bent a plurality of times. Thus, the heat generating area per unit area of the heating portion 116 can be increased.

The first connection portion 113 may be formed at an end of the heating portion 116. The second connection portion 115 may be formed at another end of the heating portion 116. The first connection portion 113 may connect a first pad electrode 112 and the heating portion 116. The second connection portion 115 may connect a second pad electrode 114 and the heating portion 116. The heating electrode 110 may be formed integrally with the heating portion 116, the connecting portions 113 and 115, and the pad electrodes 112 and 114.

Figure 3:
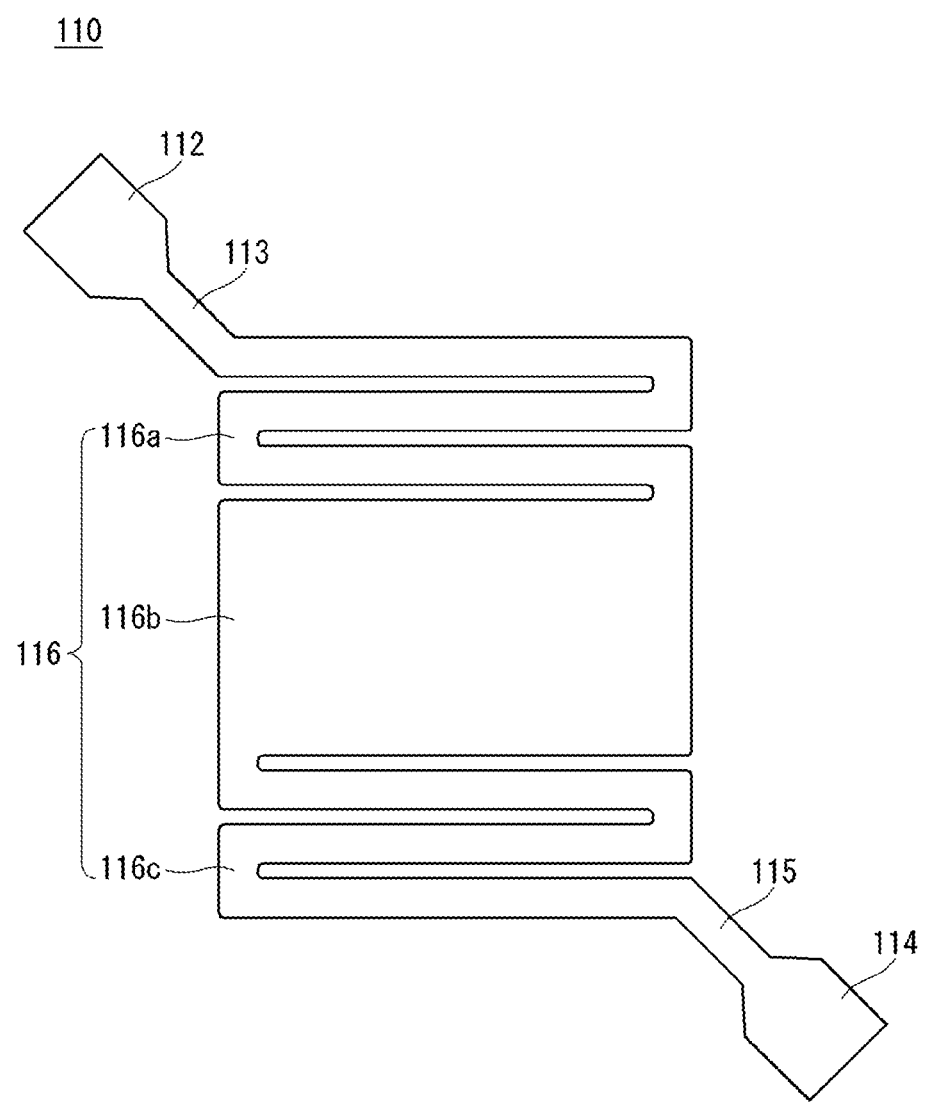

Referring to FIG. 3, the heating portion 116 may include a flat portion 116b and winding portions 116a and 116c. The flat portion 116b may be a thin plate. The winding portions 116a and 116c may include a first winding portion 116a and a second winding portion 116c. The first winding portion 116a may be connected to a side of the flat portion 116b. And the second winding portion 116c may be connected to another side of the flat portion 116b. The flat portion 116b may be positioned between the first winding portion 116a and the second winding portion 116c. The flat portion 116b, the first winding portion 116a, and the second winding portion 116c may be integrally formed.

Figure 4:
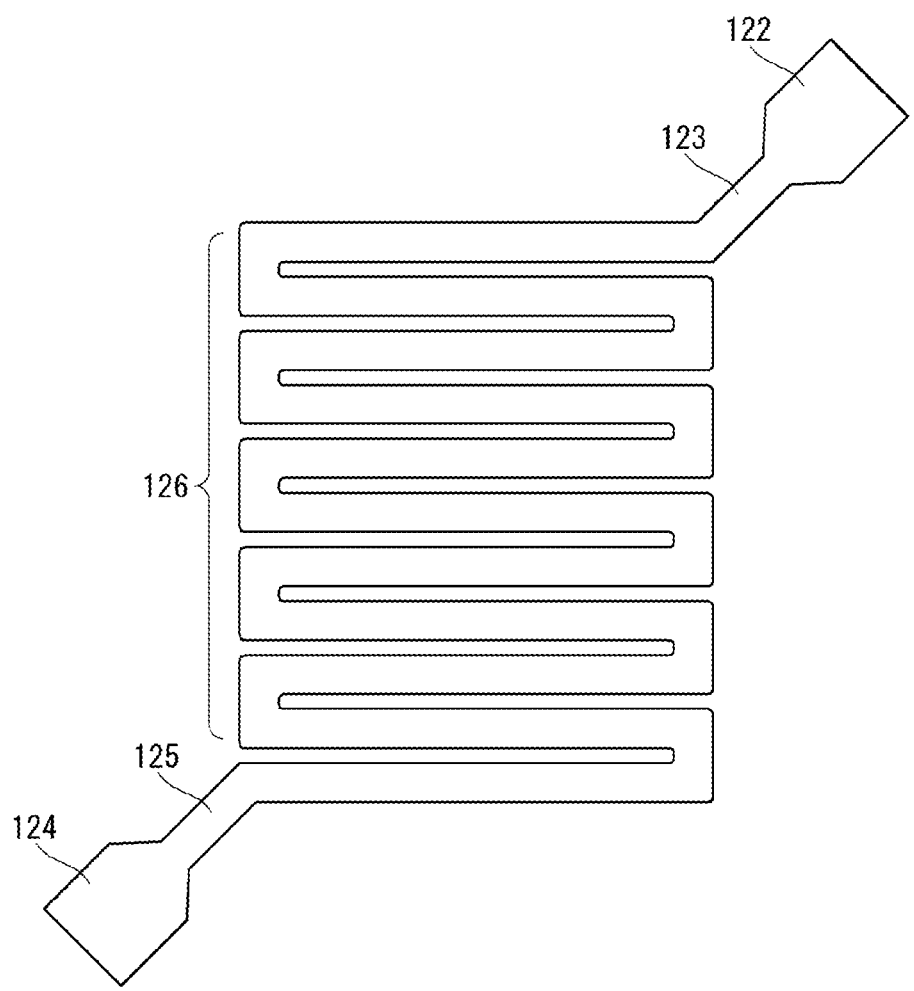

Referring to FIG. 4, the electrode 120 may be a sensing electrode 120. The electrode 120 may be referred to as a first electrode 120. The sensing electrode 120 may include an extension portion 126, and connection portions 123 and 125. The extension portion 126 may be formed of a metal having a resistance. For example, the resistance of extension portion 126 may be several hundred kilo ohms. The extension portion 126 can be wound. The extension portion 126 may be bent a plurality of times. Accordingly, the sensing area per unit area of the extension portion 126 can be increased.

The first connection portion 123 may be formed at an end of the extension portion 126. The second connection portion 125 may be formed at another end of the extension portion 126. The first connection portion 123 may connect a first pad electrode 122 and the extension portion 126. The second connection portion 125 may connect a second pad electrode 124 and the extension portion 126. The extension portion 126, the connection portions 123 and 125, and the pad electrodes 122 and 124 may be formed integrally.

Figure 5:
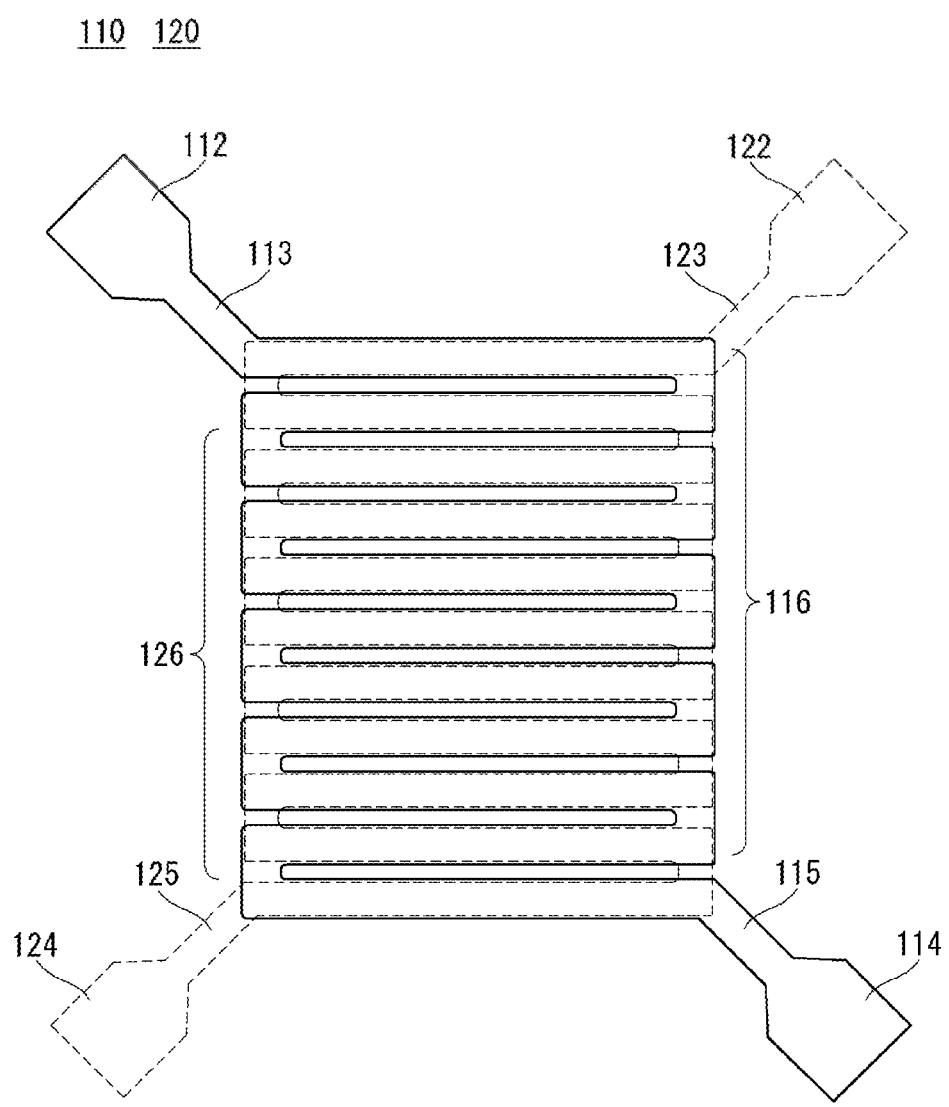

Referring to FIG. 5, the heating electrode 110 and the sensing electrode 120 may overlap each other. Accordingly, the heating electrode 110 can provide heat to the sensing electrode 120, and the sensing electrode 120 can detect or sense the gas at a certain temperature.

Figure 6:
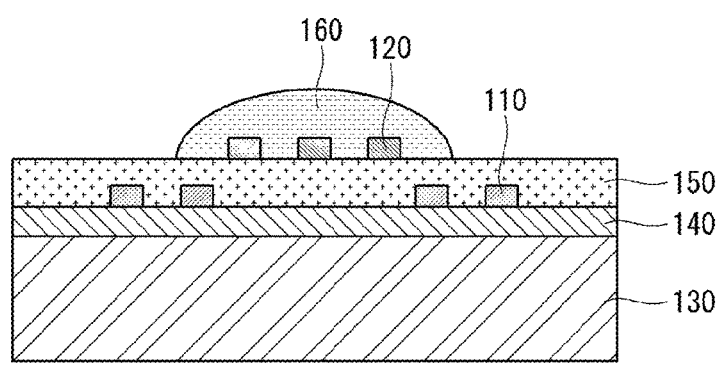
FIGS. 6 and 7 are views showing examples of cross sections of a gas sensor according to an embodiment of the present invention.
Figure 7:
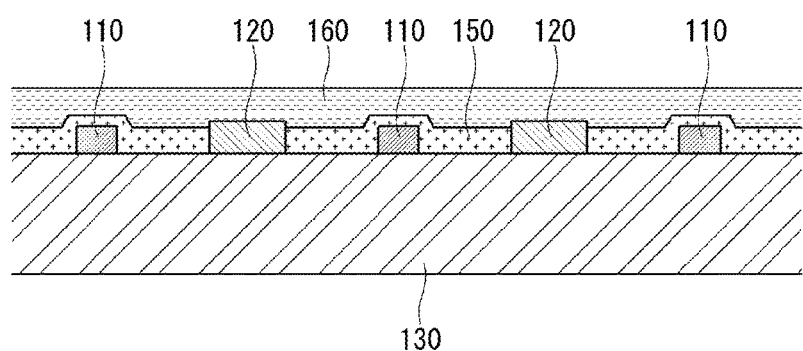

FIGS. 6 and 7 are views showing examples of cross sections of a gas sensor according to an embodiment of the present invention.

Referring to FIG. 6, a heating electrode 110 may be formed on the substrate 130. An electric insulating layer 150 may be formed on the heating electrode 110. The electric insulating layer 150 may cover the heating electrode 110. The sensing electrode 120 may be formed on the electric insulating layer 150. The sensing electrode 120 may form a layer different from the heating electrode 110. The sensing electrode 120 may be electrically separated from the heating electrode 110 by an insulating film 150. The sensing electrode 120 and the heating electrode 110 may not meet each other.

The sensing portion 160 may be formed on the upper side of the sensing electrode 120. The sensing portion 160 may cover at least a part of the sensing electrode 120. In addition, the sensing portion 160 may cover a part of the electric insulating layer 150. The heat insulating layer 140 may be formed between the heating electrode 110 and the substrate 130. The heat insulating layer 140 may be positioned between the electric insulating layer 150 and the substrate 130.

Referring to FIG. 7, the heating electrode 110 may be formed on the upper side of the substrate 130. The sensing electrode 120 may be formed on the upper side of the substrate 130. The sensing electrode 120 may be located on the left or right side of the heating electrode 110. The sensing electrode 120 may be disposed horizontally with the heating electrode 110. The sensing electrode 120 may be located on the same layer as the heating electrode 110.

An electric insulating layer 150 may be formed between the heating electrode 110 and the sensing electrode 120. The electric insulating layer 150 may electrically isolate the heating electrode 110 from the sensing electrode 120. The electric insulating layer 150 may cover the entirety of the heating electrode 110. On the other hand, the electric insulating layer 150 may cover a part of the sensing electrode 120. At least a part of the sensing electrode 120 may be exposed to the outside of the electric insulating layer 150.

The sensing portion 160 may be formed on the electric insulating layer 150. The sensing portion 160 may be formed on the upper side of the sensing electrode 120. The sensing portion 160 may be electrically connected to the sensing electrode 120. The sensing portion 160 may be electrically separated from the heating electrode 110 by an electric insulating layer 150.

FIGS. 8 to 14 are views showing examples of a gas sensor according to an embodiment of the present invention.

Figure 8:
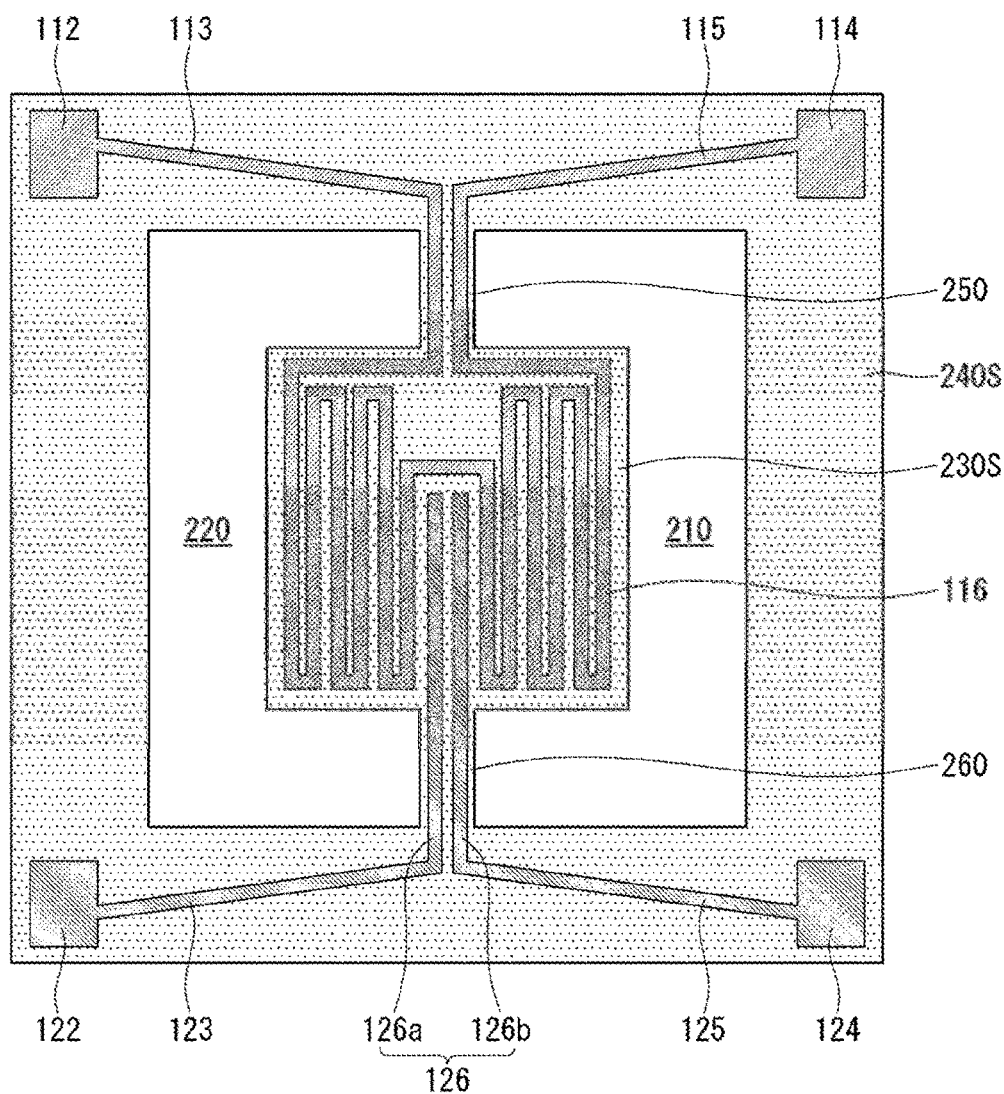
FIGS. 8 to 14 are views showing examples of a gas sensor according to an embodiment of the present invention.

Referring to FIG. 8, the substrate 200 may have a generally rectangular shape. The substrate 200 may be an electric insulator. The substrate 200 may include openings 210 and 220. The openings 210 and 220 may be generally rectangular in shape. The opening 210 and 220 may be a plurality of openings 210 and 220. The first opening 210 may be formed on the plane of the substrate 200 and may be formed on the right side of the plane of the substrate 200. The second opening 220 may be formed in the left side of the substrate 200. The first opening 210 may be symmetrical with the second opening 220.

In another aspect, the substrate 200 may include an inner substrate 230S and an outer substrate 240S. The outer substrate 240S may have an empty space at the center thereof. The inner substrate 230S may be located inside the outer substrate 240S. The inner substrate 230S may be located in the empty space. The inner substrate 230S may be spaced apart from the outer substrate 240S. The outer substrate 240S may be spaced apart from the inner substrate 230S by a certain distance.

The bridge 250 and 260 can connect the outer substrate 240S and the inner substrate 230S. The bridge 250 and 260 may include a plurality of bridges 250 and 260. The first bridge 250 may connect the upper end of the inner substrate 230S and the lower end of the upper portion of the outer substrate 240S. The second bridge 260 may connect the lower end of the inner substrate 230S and the upper end of the lower portion of the outer substrate 240S.

The heating electrode 110 (see FIG. 7) may be formed on the upper surface of the substrate 200. The heating portion 116 may be formed on the upper surface of the inner substrate 230S. The pad electrodes 112 and 114 may be formed on the upper surface of the outer substrate 240S. The pad electrodes 112 and 114 may be positioned adjacent to the upper corner of the outer substrate 240S. The first pad electrode 112 may be positioned adjacent to the left corner of the upper portion of the outer substrate 240S. The second pad electrode 114 may be positioned adjacent to the right corner of the upper portion of the outer substrate 240S. The upper surface of the substrate 200 may stand for a surface of the substrate 200. The upper and lower portions of the substrate 200 may stand for relative positions on the surface of the substrate 200. The upper and lower corners of the substrate 200 may stand for a relative position on the surface of the substrate 200. The left and right sides of the substrate 200 may indicate relative positions on the surface of the substrate 200.

The first connection portion 113 may connect the heating portion 116 and the first pad electrode 112. A part of the first connection portion 113 may be formed at an upper of the first bridge 250. The first connection portion 113 extends from the heating portion 116 at the upper portion of the outer substrate 240S, is formed on the upper part of the first bridge 250, lead to the first pad electrode 112.

The second connection portion 115 may connect the heating portion 116 and the second pad electrode 114. A part of the second connection portion 115 may be formed at an upper of the first bridge 250. The second connection portion 115 extends from the heating portion 116 at the upper portion of the outer substrate 240S, is formed on the upper part of the first bridge 250, lead to the second pad electrode 114.

The sensing electrode 120 (see FIG. 7) may be formed on the upper surface of the substrate 200. The extension portion 126 may be formed on the upper surface of the inner substrate 230S. The extension portion 126 may be elongated and formed. The extension portion 126 may not folded nor wound or bent. The extension portion 126 may be formed a nearly straight line.

The extension portion 126 may include a plurality of extension portions 126. The extension portion 126 may include a first extension portion 126a and a second extension portion 126b. The first extension portion 126a may be formed adjacent to the heating portion 116 of the heating electrode 110. The first extension portion 126a may be formed on the upper surface of the inner substrate 230S. The first extension portion 126a may extend straight while being surrounded by the heating portion 116 of the heating electrode 110.

The second extension portion 126b may be formed beside the first extension portion 126a and may have the same shape. The second extension portion 126b may be parallel to the first extension portion 126a. Alternatively, the second extension portion 126b may be disposed with a slight inclination with respect to the first extension portion 126a.

The first extension portion 126a and the second extension portion 126b may be spaced apart from each other. The first pad electrode 122 may be electrically connected to the first extension portion 126a. The first pad electrode 122 may be formed on a corner of the upper surface of the outer substrate 240S. The second pad electrode 124 may be formed on another corner of the upper surface of the outer substrate 240S.

The first connection portion 123 may connect the first pad electrode 122 and the first extension portion 126a. The second connection portion 125 may connect the second pad electrode 124 and the second extension portion 126b. For example, the first connection portion 123 may be connected to the first extension portion 126a on the inner substrate 230S, a part of the first connection portion 123 may be formed on the upper surface of the second bridge 260, and the first connection portion 123 may be connected to the first pad electrode 122 on the outer substrate 240S.

For example, the second connection portion 123 may be connected to the second extension portion 126b on the inner substrate 240S, a part of the second connection portion 125 may be formed on the upper surface of the second bridge 260, and the second connection portion 125 may be connected to the second pad electrode 124 on the outer substrate 240S.

After the heating electrode 110 is formed on the substrate 200, an insulating layer (not shown) may be formed on the heating electrode 110. The insulating layer can prevent the heat generated from the heating electrode 110 from easily dissipating to the outside, and can improve the durability of the heating electrode 110. The insulating layer formed on the upper surface of the heating electrode 110 and the substrate 200 may improve heat insulating property and stability of the gas sensor. The sensing electrode 120 may be insulated from the heating electrode 110 by the insulating layer. The insulating layer may mean an electric insulating layer and/or a thermal (heat) insulating layer.

Figure 9:
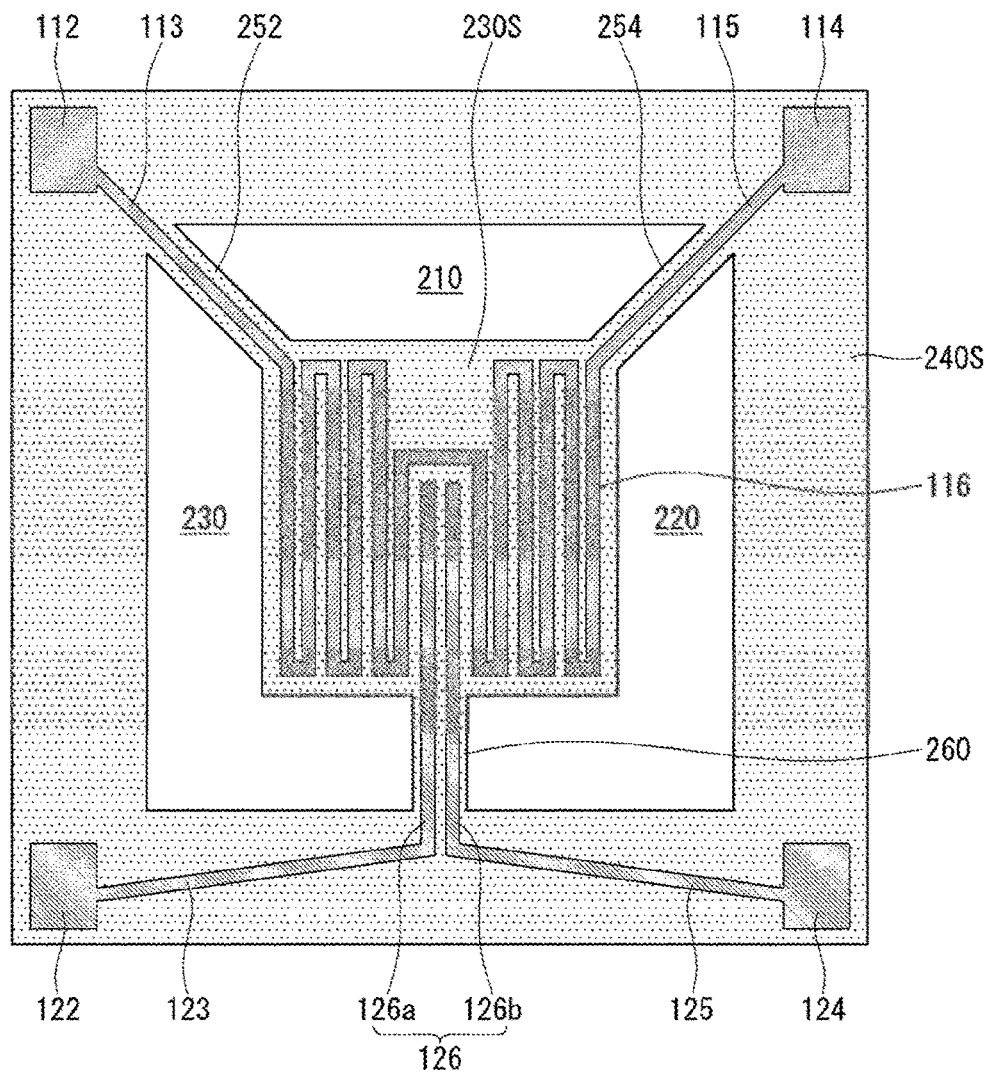

Referring to FIG. 9, the opening 210, 220, and 230 may include a plurality of openings 210, 220, and 230. The first opening 210 may be formed at the upper portion of the substrate 200. The second opening 220 may be formed at the right side of the substrate 200. The third opening 230 may be formed at the left side of the substrate 200. The second opening 220 and the third opening 230 may face each other. The second opening 220 and the third opening 230 may be symmetrical.

In another point of view, the bridge 252, 254, and 260 can connect the inner substrate 230S and the outer substrate 240S. The bridge 252, 254, and 260 may include a plurality of bridges 252, 254, and 260. The first bridge 252 may be located at the upper left corner of the inner substrate 230S. The first bridge 252 may extend from the upper left corner of the inner substrate 230S to the outer substrate 240S. The second bridge 254 may be located at the upper right corner of the inner substrate 230S. The second bridge 254 may extend from the upper right corner of the inner substrate 230S to the outer substrate 240S. The third bridge 260 may extend from the lower end of the inner substrate 230S to the outer substrate 240S.

The first connection portion 113 of the heating electrode 110 may connect the heating portion 116 to the first pad electrode 112 through the first bridge 252. The second connection portion 115 of the heating electrode 110 may connect the heating portion 116 to the second pad electrode 114 through the second bridge 254.

The first connection portion 123 of the sensing electrode 120 may connect the heating portion 116 to the first pad electrode 122 through the third bridge 260. The second connection portion 125 of the sensing electrode 120 may connect the heating portion 116 to the second pad electrode 124 through the third bridge 260.

Figure 10:
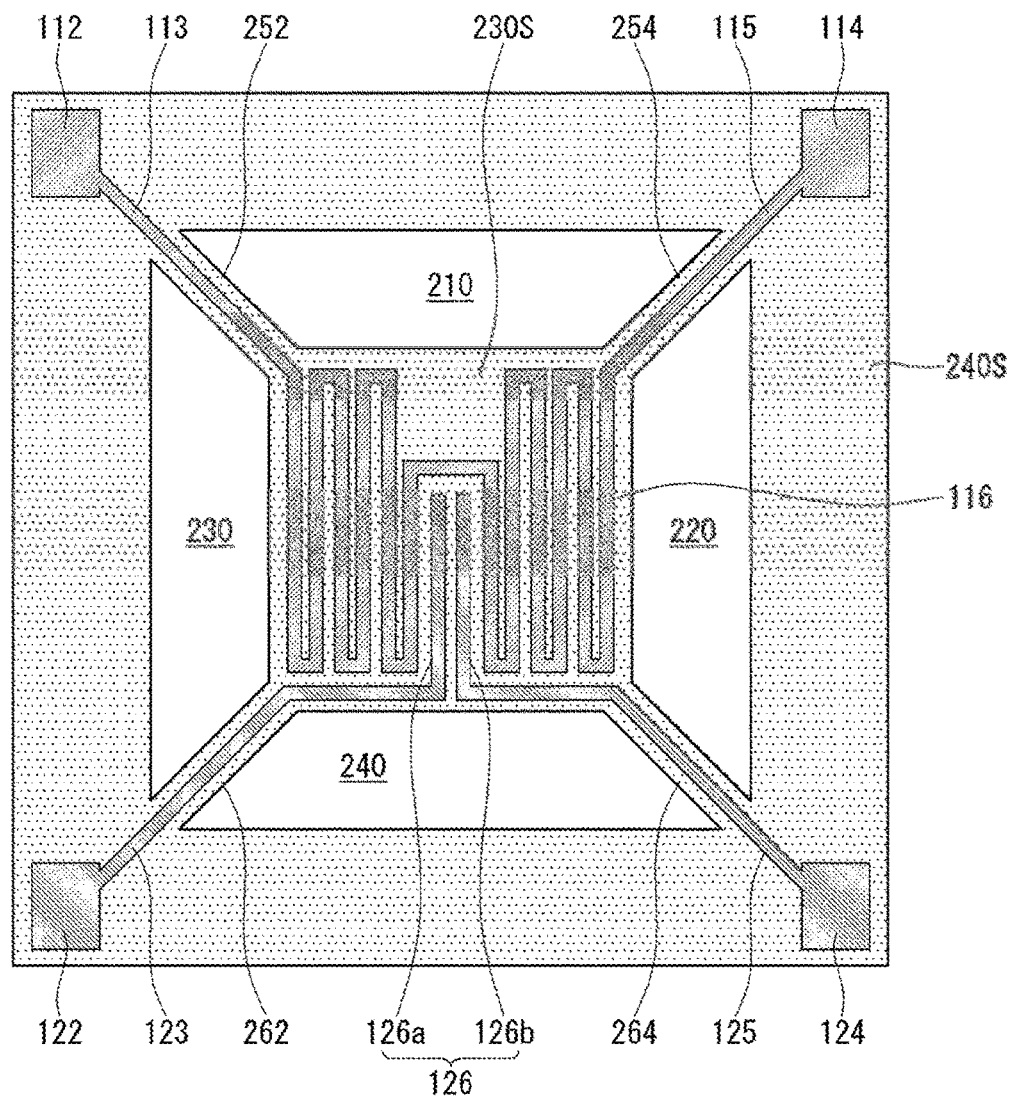

Referring to FIG. 10, the opening 210, 220, 230, and 240 may include a plurality of openings 210, 220, 230, and 240.

The first opening 210 may be formed at the upper portion of the substrate 200. The second opening 220 may be formed at the right side of the substrate 200. The third opening 230 may be formed at the left side of the substrate 200. The fourth opening 240 may be formed at the lower portion of the substrate 200.

The first opening 210 and the fourth opening 240 may face each other or may be symmetrical. The second opening 220 and the third opening 230 may face each other or may be symmetrical.

In another point of view, the bridge 252, 254, 262, and 264 can connect the inner substrate 230S and the outer substrate 240S. The bridge 252, 254, 262, 264 may include a plurality of bridges 252, 254, 262,264.

The first bridge 252 may be located at the upper left corner of the inner substrate 230S. The first bridge 252 may extend from the upper left corner of the inner substrate 230S to the outer substrate 240S. The second bridge 254 may be located on the upper right corner of the inner substrate 230S. The second bridge 254 may extend from the upper right corner of the inner substrate 230S to the outer substrate 240S. The third bridge 262 may be located at the lower left corner of the inner substrate 230S. The third bridge 262 may extend from the lower left corner of the inner substrate 230S to the outer substrate 240S. The fourth bridge 264 may be located at the lower right corner of the inner substrate 230S. The fourth bridge 264 may extend from the lower right corner of the inner substrate 230S to the outer substrate 240S.

The first connection portion 113 of the heating electrode 110 may connect the heating portion 116 to the first pad electrode 112 through the first bridge 252. The second connection portion 115 of the heating electrode 110 may connect the heating portion 116 to the second pad electrode 114 through the second bridge 254.

The first connection portion 123 of the sensing electrode 120 may connect the heating portion 116 to the first pad electrode 122 through the third bridge 262. The second connection portion 125 of the sensing electrode 120 may connect the heating portion 116 to the second pad electrode 124 through the fourth bridge 264.

Figure 11:
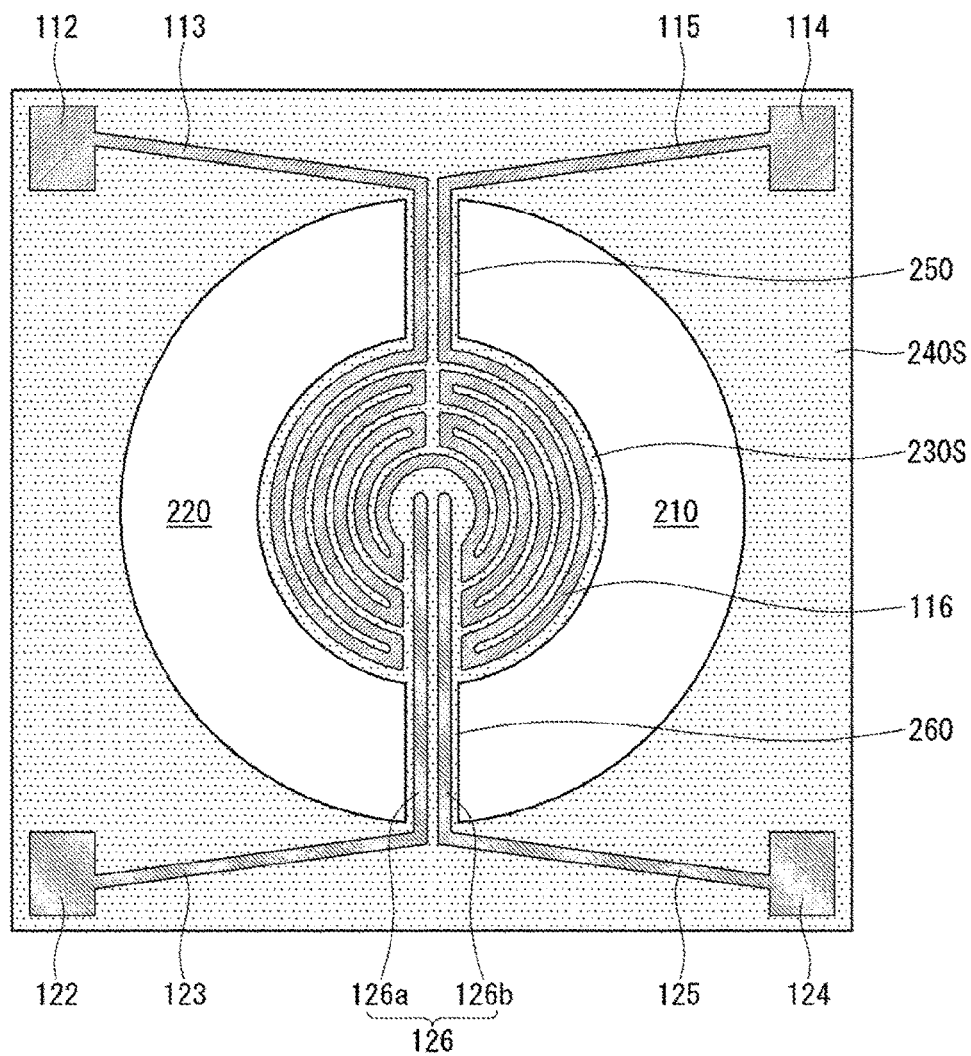

Referring to FIG. 11, the inner substrate 230S may be circular. The outer substrate 240S may be rectangular. The central portion of the outer substrate 240S can form a circular hollow space. The inner substrate 230S may be located in the hollow space.

The substrate 200 may include opening 210 and 220. The opening 210 and 220 may include a plurality of openings 210 and 220. The first opening 210 may be located on the right side of the inner substrate 230S. The second opening 220 may be located on the left side of the inner substrate 230S. The first opening 210 may face the second opening 220. The first opening 210 may be symmetrical with the second opening 220.

In another point of view, the bridge 250 and 260 can connect a part of the inner substrate 230S and a part of the outer substrate 240S. The bridge 250 and 260 may include a plurality of bridges 250 and 260. The first bridge 250 can connect the upper portion of the inner substrate 230S and the inner side of the outer substrate 240S. The second bridge 260 can connect the lower portion of the inner substrate 230S and the inner side of the outer substrate 240S. The first bridge 250 may be symmetrical with the second bridge 260 with respect to the inner substrate 230S. The inner substrate 230S may be positioned between the first bridge 250 and the second bridge 260.

Figure 12:
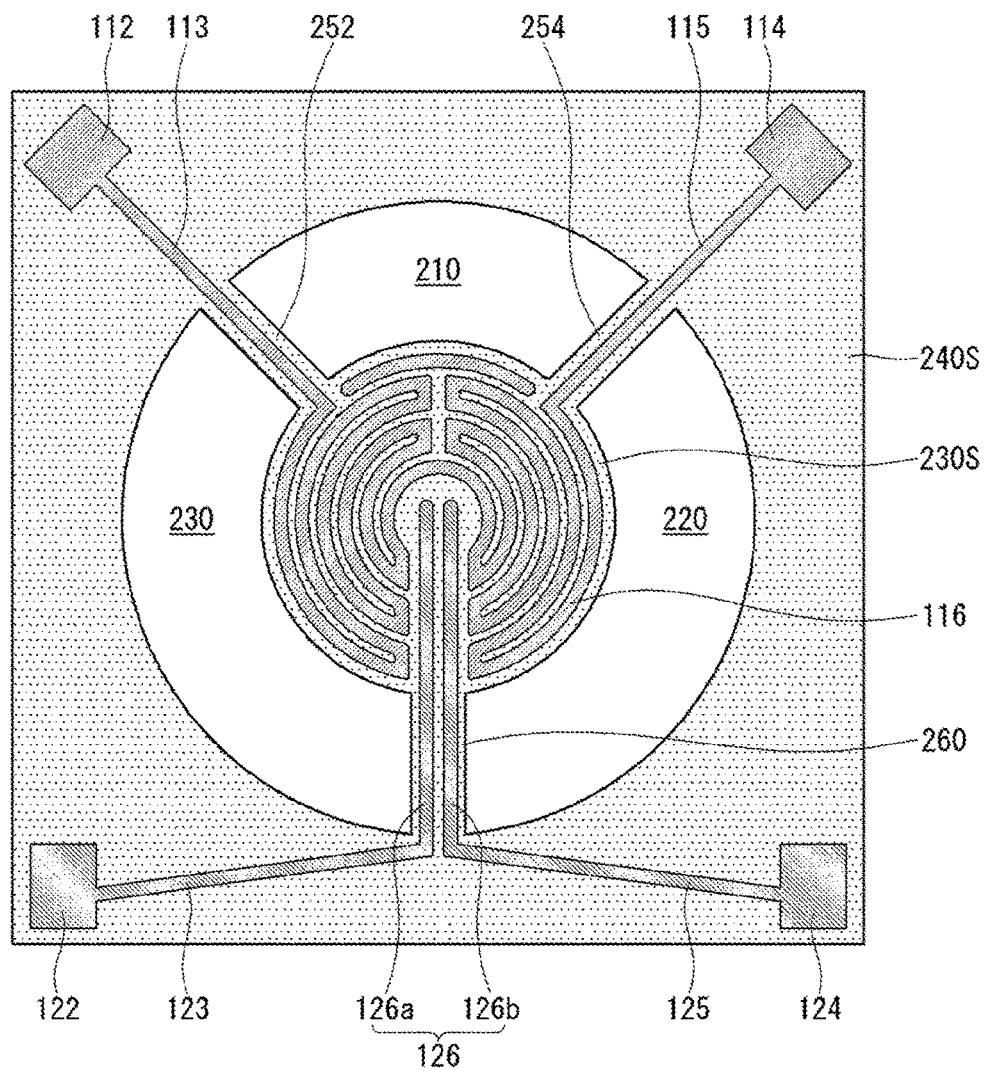

Referring to FIG. 12, the substrate 200 may include opening 210, 220, and 230. The opening 210, 220, and 230 may include a plurality of openings 210, 220, and 230. The first opening 210 may be located at the upper of the inner substrate 230S. The second opening 220 may be located at the right side of the inner substrate 230S. The third opening 230 may be located at the left side of the inner substrate 230S.

In other point of view, the bridge 252, 254, and 260 may connect a part of the inner substrate 230S and a part of the outer substrate 240S. The bridge 252, 254, and 260 may include a plurality of bridges 252, 254, and 260. The first bridge 252 can connect the upper left side of the inner substrate 230S and the inner side of the outer substrate 240S. The second bridge 254 can connect the upper right side of the inner substrate 230S and the inner side of the outer substrate 240S. The third bridge 260 can connect the lower portion of the inner substrate 230S and the inner side of the outer substrate 240S.

Figure 13:
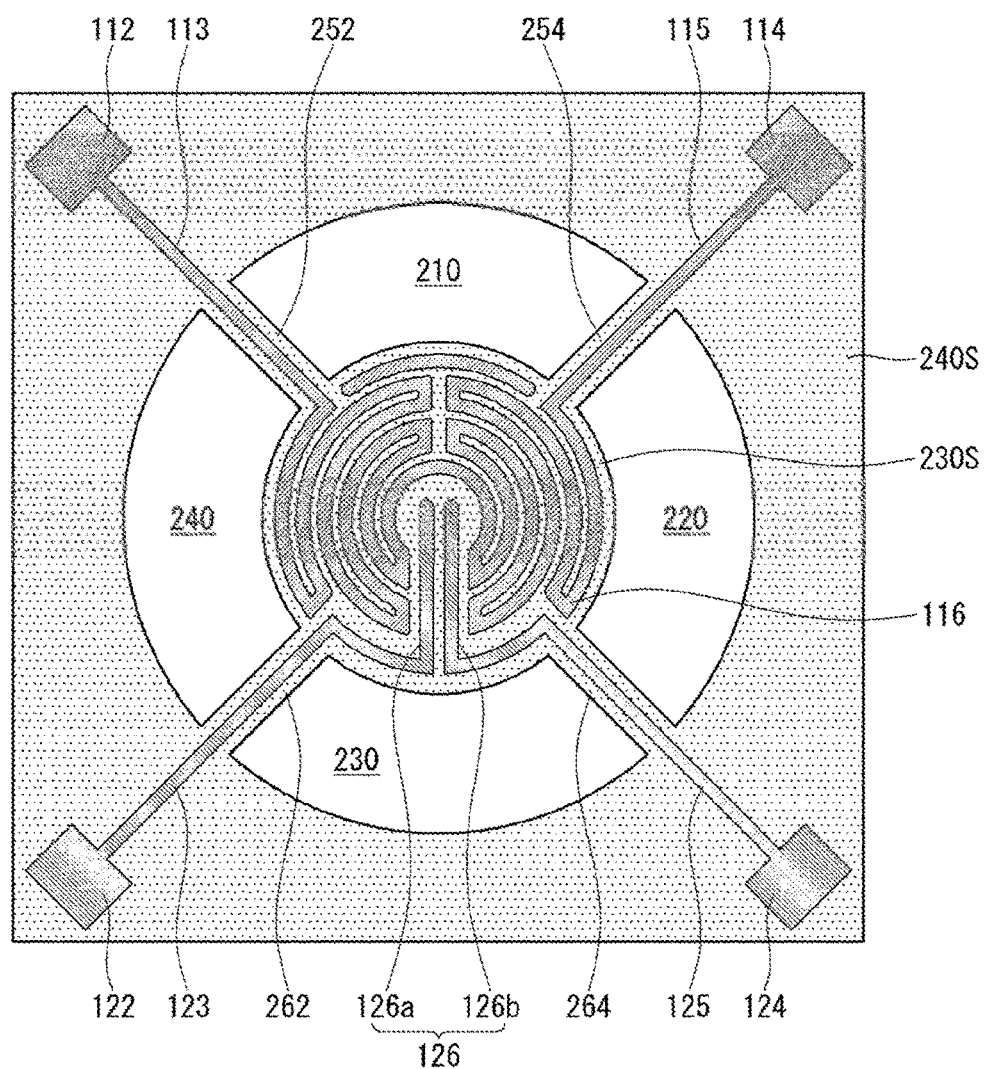
Figure 14:
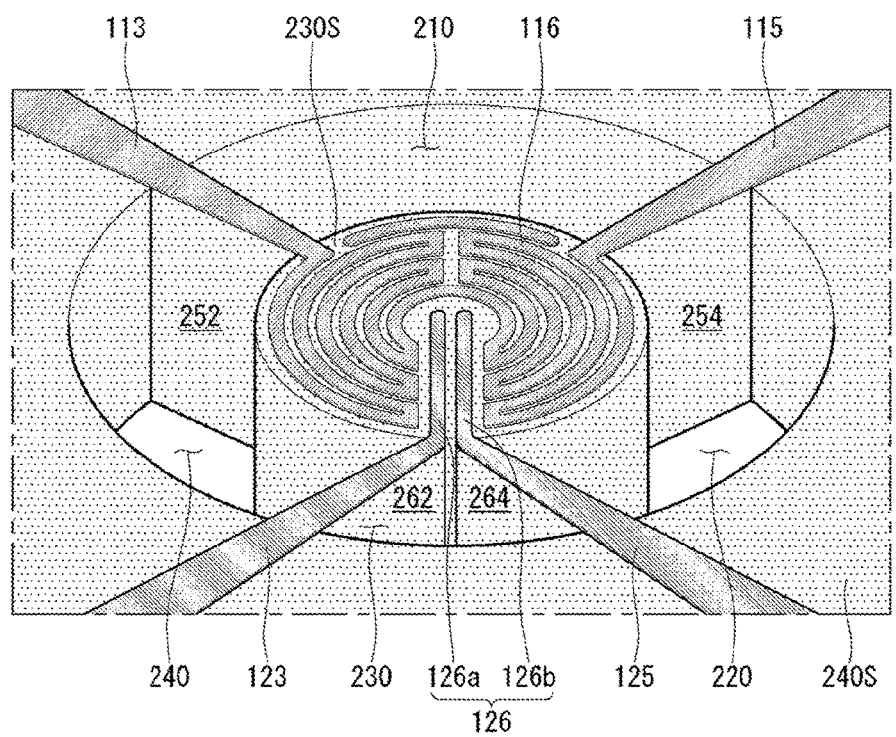

Referring to FIGS. 13 and 14, the substrate 200 may include opening 210, 220, 230 and 240. The opening 210, 220, 230, 240 may include a plurality of openings 210, 220, 230, 240. The first opening 210 may be located at the upper of the inner substrate 230S. The second opening 220 may be located at the right of the inner substrate 230S. The third opening 230 may be located at the lower of the inner substrate 230S. The fourth opening 240 may be located at the left of the inner substrate 240S.

In another point of view, the bridge 252, 254, 262, and 264 can connect a part of the inner substrate 230S and a part of the outer substrate 240S. The bridge 252, 254, 262, and 264 may include a plurality of bridges 252, 254, 262, and 264. The first bridge 252 can connect the upper left portion of the inner substrate 230S and the inner side of the outer substrate 240S. The second bridge 254 can connect the upper right portion of the inner substrate 230S and the inner side of the outer substrate 240S. The third bridge 262 can connect the lower left portion of the inner substrate 230S and the inner side of the outer substrate 240S. The fourth bridge 264 can connect the lower right portion of the inner substrate 230S and the inner side of the outer substrate 240S.

The sensing portion 160 (see FIG. 7) may be positioned on the front surface of the inner substrate 230S. The front surface of the inner substrate 230S may refer to a surface of the inner substrate 230S on which the electrodes 110 and 120 are disposed. The sensing portion 160 (see FIG. 7) may be formed on the front surface of the heating electrode 110 or the sensing electrode 120. The sensing unit 160 (see FIG. 7) may cover at least a portion of the heating electrode 110 or the sensing electrode 120. The electrodes 110 and 120 may be positioned between the inner substrate 230S and the sensing unit 160 (see FIG. 7).

The first extension portion 126a of the sensing electrode 120 may be electrically connected to the second extension portion 126b. The sensing portion 160 (see FIG. 7) may connect the first extension portion 126a and the second extension portion 126b electrically.

Figure 15:
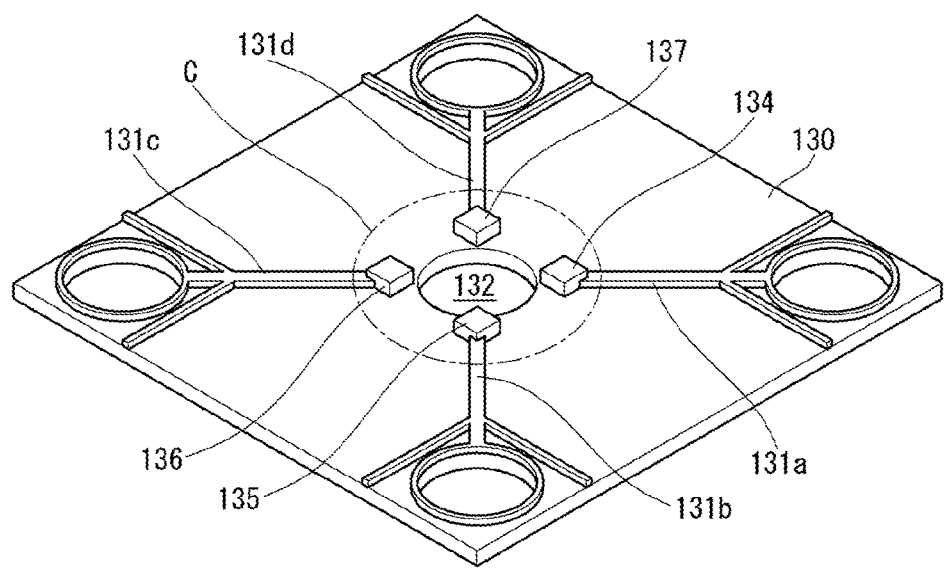
FIGS. 15 to 18 illustrate examples of a gas sensor package substrate according to an embodiment of the present invention.
Figure 16:
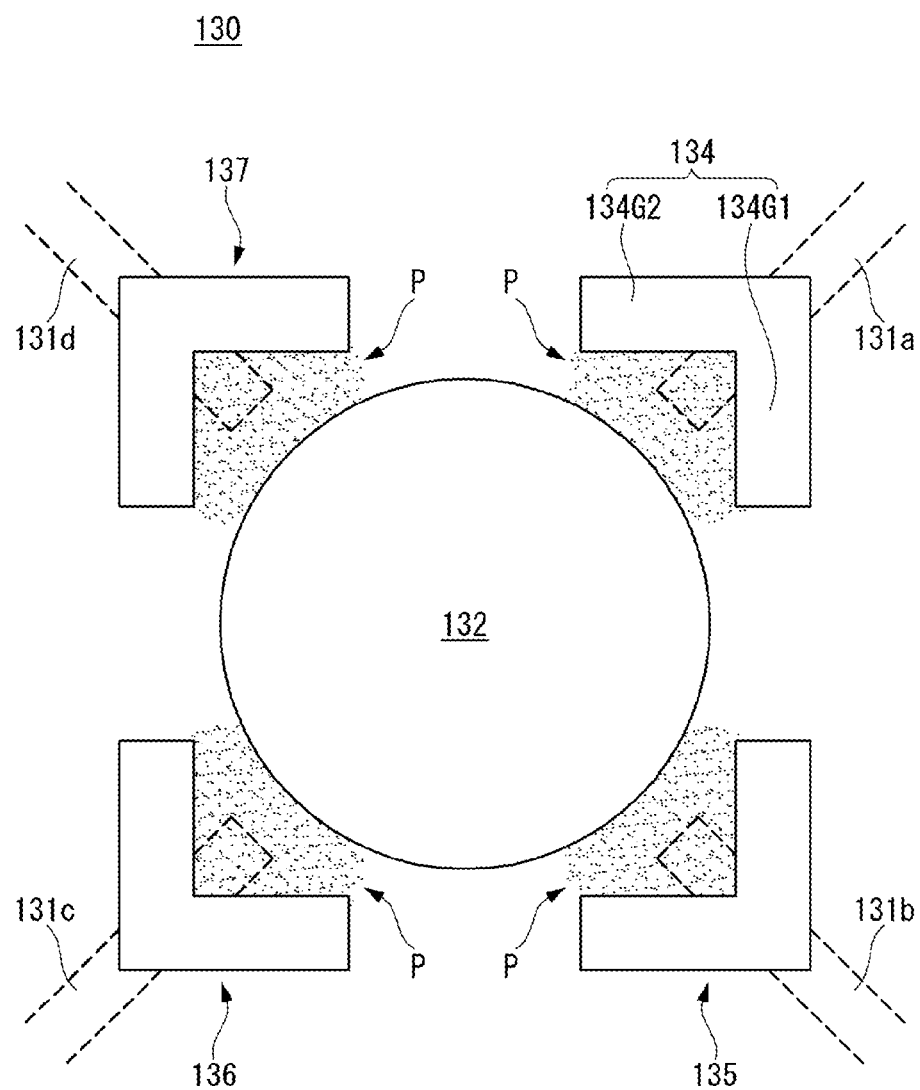
Figure 17:
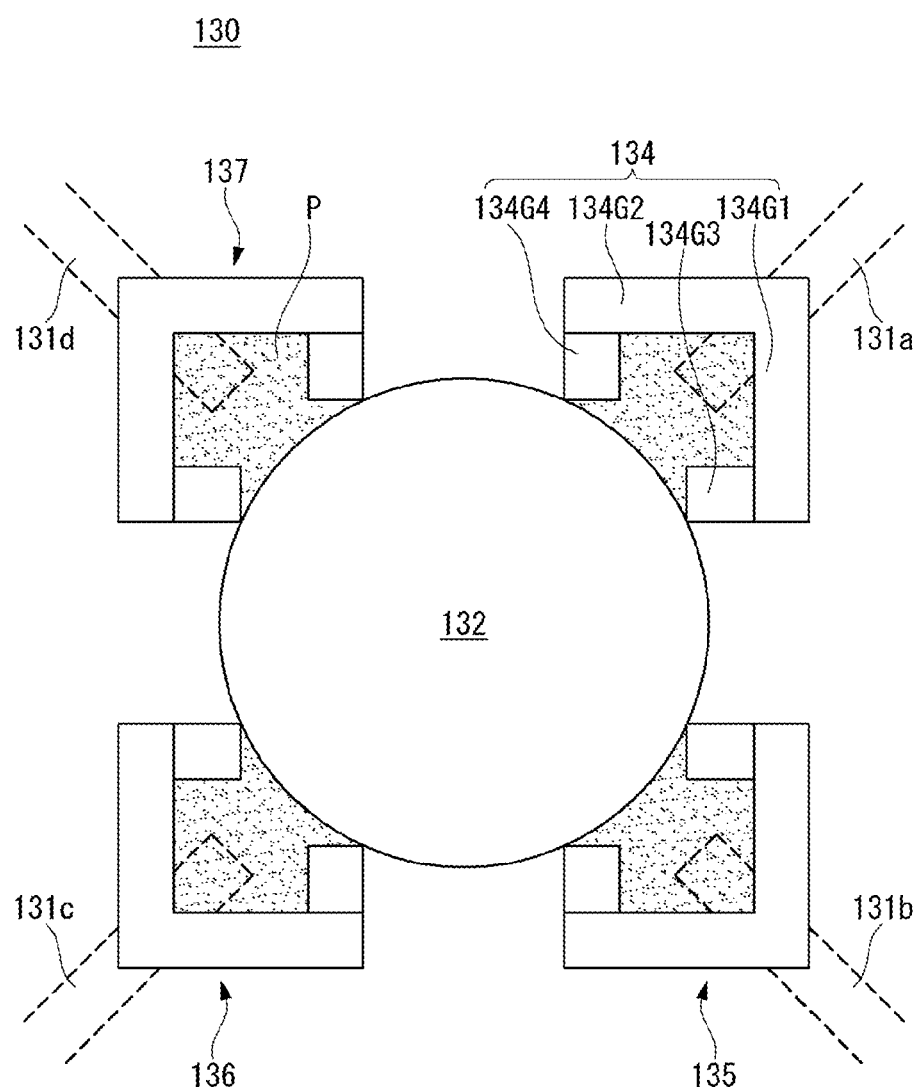
Figure 18:
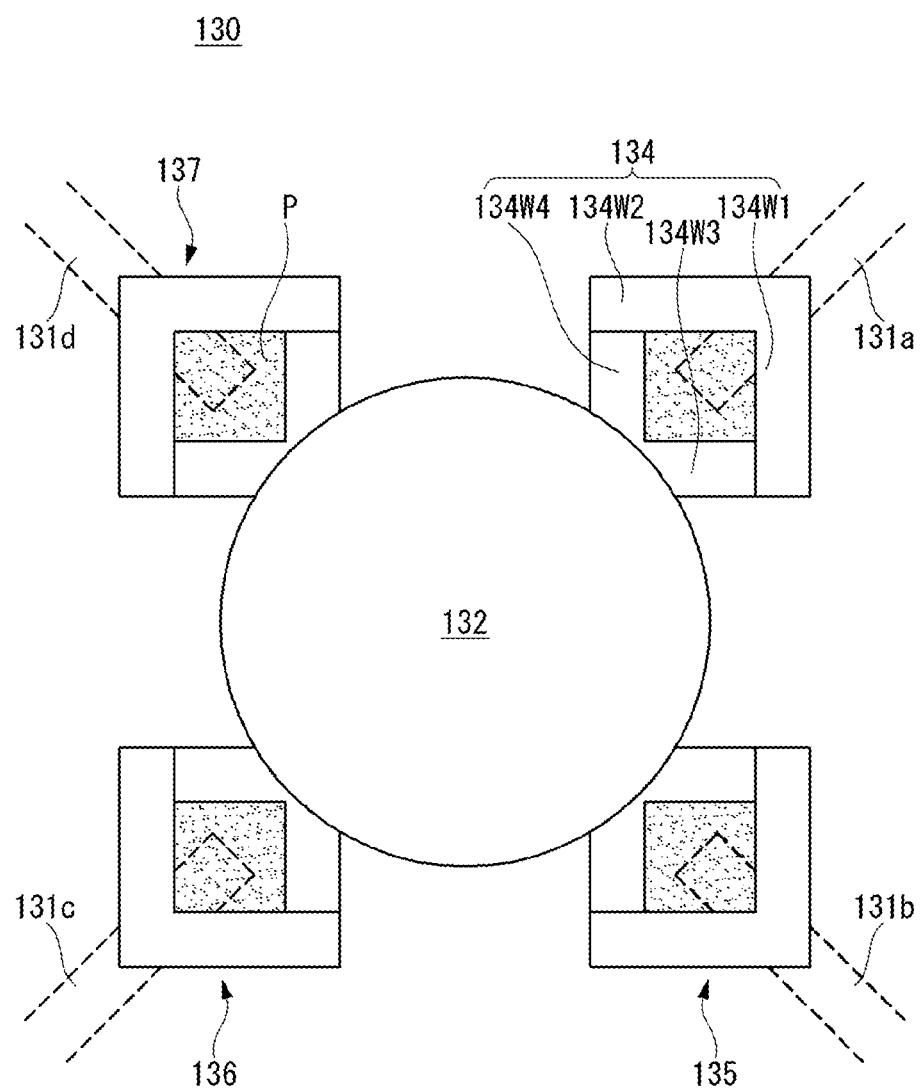

FIGS. 15 to 18 are views showing examples of a gas sensor package substrate according to an embodiment of the present invention. FIGS. 16 to 18 are views showing examples of enlargement of the area C of FIG. 15.

Referring to FIG. 15, the substrate 130 may have an opening 132 at the center thereof. The opening 132 may go through the substrate 130. The bonding pads 134, 135, 136, and 137 may be formed around the opening 132. The bonding pads 134, 135, 136, and 137 may be metal electrodes. The substrate 130 may include a plurality of bonding pads 134, 135, 136, and 137. The number of the bonding pads 134, 135, 136, and 137 may be four. The four bonding pads 134, 135, 136, and 137 may be sequentially positioned around the opening 132.

The first bonding pad 134, the second bonding pad 135, the third bonding pad 136 and the fourth bonding pad 137 may be sequentially formed adjacent to the opening 132 on the substrate 130.

The first electrode line 131a may be connected to the first bonding pad 134, the second electrode line 131b may be connected to the second bonding pad 135 and the third electrode line 131c may be connected to the third bonding pad 136 and the fourth electrode line 131d may be connected to the fourth bonding pad 137.

Referring to FIG. 16, the first bonding pad 134 may include a first guide 134G1 and a second guide 134G2. The first guide 134G1 may be connected to the second guide 134G2. The first guide 134G1 and the second guide 134G2 may be positioned adjacent to the opening 132 of the substrate 130. The first guide 134G1 and the second guide 134G2 may have a generally bent shape. For example, the first guide 134G1 and the second guide 134G2 may form an overall '¬' or 'ㄴ' shape. The descriptions of the second bonding pad 135 to the fourth bonding pad 137 are the same as the first bonding pad 134.

The metal paste may be placed between the first guide 134G1, the second guide 134G2, and the opening 132. The heights of the first to fourth bonding pads 134, 135, 136, and 137 may be greater than the heights of the first to fourth electrode lines 131a, 131b, 131c, and 131d.

The above arrangement of the bonding pads 134, 135, 136, and 137 and the electrode lines 131a, 131b, 131c, and 131d may make the second substrate 200 (see FIG. 14) aligned on right location and prevent electric short between bonding pads or between pad electrodes, when the second substrate 200 (see FIG. 14) accompanying the sensing portion 160 (see FIG. 7) is fixed to the first substrate 130 via flip-chip bonding.

Referring to FIG. 17, the first bonding pad 134 may include a first guide 134G1, a second guide 134G2, a third guide 134G3, and a fourth guide 134G4. The third guide 134G3 may extend from the first guide 134G1 toward the opening 132 of the first substrate 130. The fourth guide 134G4 may extend from the second guide 134G2 toward the opening 132 of the first substrate 130. The first guide 134G1 to the fourth guide 134G4 may form a C-shape as a whole.

The heights of the first guide 134G1 and the second guide 134G2 may be the same. The height of the third guide 134G3 and the fourth guide 134G4 may be the same. At this time, the height of the first guide 134G1 and the second guide 134G2 may be different from the height of the third guide 134G3 and the fourth guide 134G4. For example, the height of the first guide 134G1 may be greater than the height of the third guide 134G3, and the height of the second guide 134G2 may be greater than the height of the fourth guide 134G4. The bonding pad 134 may form a stepped portion. The stepped portion at the bonding pad 134 may be formed in a direction in which the bonding pad 134 is extended.

Accordingly, the metal paste P may be positioned inside the bonding pads 134, 135, 136, 137 and prevented from spreading to the outside of the bonding pads 134, 135, 136, 137, thereby preventing electrical short between the bonding pads or between the pad electrodes.

In other words, the second substrate 200 (see FIG. 14) may be aligned on right location and electric short between bonding pads or between pad electrodes may be prevented, when the second substrate 200 (see FIG. 14) accompanying the sensing portion 160 (see FIG. 7) is fixed to the first substrate 130 via flip-chip bonding.

Referring to FIG. 18, the first bonding pad 134 may have a first wall 134W1, a second wall 134W2, a third wall 134W3, and a fourth wall 134W4. The first wall 134W1 and the second wall 134W2 may be connected to each other with the same height. The first wall 134W1 and the second wall 134W2 may have a '¬' shape or a 'ㄴ' shape as a whole. The first wall 134W1 and the second wall 134W2 may be spaced apart from the opening 132.

The third wall 134W3 and the fourth wall 134W4 may be connected to each other with the same height. The height of the first wall 134W1 and the second wall 134W2 may be greater than the height of the third wall 134W3 and the fourth wall 134W4. The third wall 134W3 and the fourth wall 134W4 may have an overall "¬" or "ㄴ" shape. The third wall 134W3 and the fourth wall 134W4 are adjacent to the opening 132 and a part of the wall 134W can be cut off by the opening 132. The inside of the corner formed by the third wall 134W3 and the fourth wall 134W4 may be spaced apart from the opening 132. As a result, the area where the metal paste P is distributed may be comparted.

The first to fourth walls 134W1, 134W2, 134W3, and 134W4 may have the overall '口' shape. The metal paste P may be surrounded inside the first to fourth walls 134W1, 134W2, 134W3, and 134W4. The metal paste P may be positioned inside the bonding pads 134, 135, 136, and 137. The first to fourth walls 134W1, 134W2, 134W3, and 134W4 can prevent the metal paste P from spreading outward of bonding pads 134, 135, 136, and 137. The first to fourth walls 134W1, 134W2, 134W3, and 134W4 can prevent an electrical short between the bonding pads or between the pad electrodes.

In other words, the second substrate 200 (see FIG. 14) may be aligned on right location and electric short between bonding pads or between pad electrodes may be prevented, when the second substrate 200 (see FIG. 14) accompanying the sensing portion 160 (see FIG. 7) is fixed to the first substrate 130 via flip-chip bonding.

FIGS. 19 to 23 are views showing examples of a gas sensor package according to an embodiment of the present invention.

Figure 19:
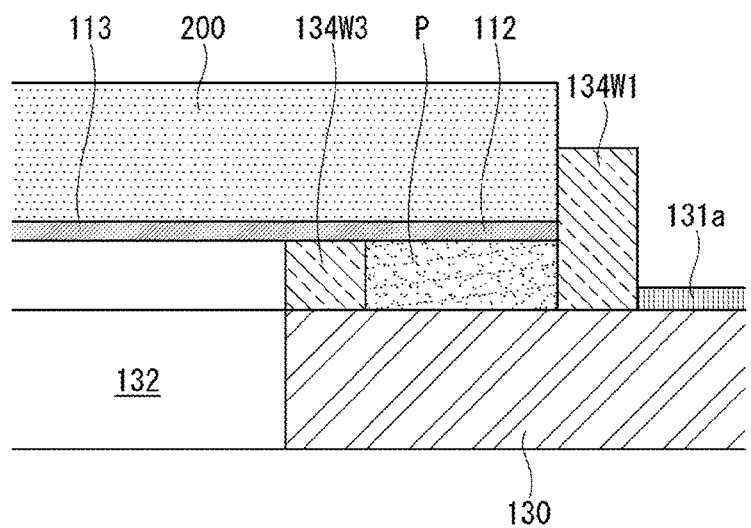
FIGS. 19 to 23 show examples of a gas sensor package according to an embodiment of the present invention.

Referring to FIG. 19, the first substrate 130 may be opposed to the second substrate 200. The surface of the first substrate 130 on which the bonding pad 134 is formed may face the surface of the second substrate 200 on which the pad electrode 112 is formed. When the second substrate 200 is placed on the first substrate 130, the second substrate 200 can be definitely aligned by the first wall 134W1 or the second wall 134W2 (see FIG. 18) of the bonding pad 134. In addition, the pad electrode 112 can be bonded to the bonding pad 134 while being in contact with the bonding pad 134. The pad electrode 112 can be bonded to the bonding pad 134 by the metal paste P. Accordingly, the pad electrode 112 can be electrically connected to the bonding pad 134.

The description of FIG. 19 can be applied not only to the embodiments of FIGS. 17 and 18 but also to the embodiment of FIG. 16.

Figure 20:
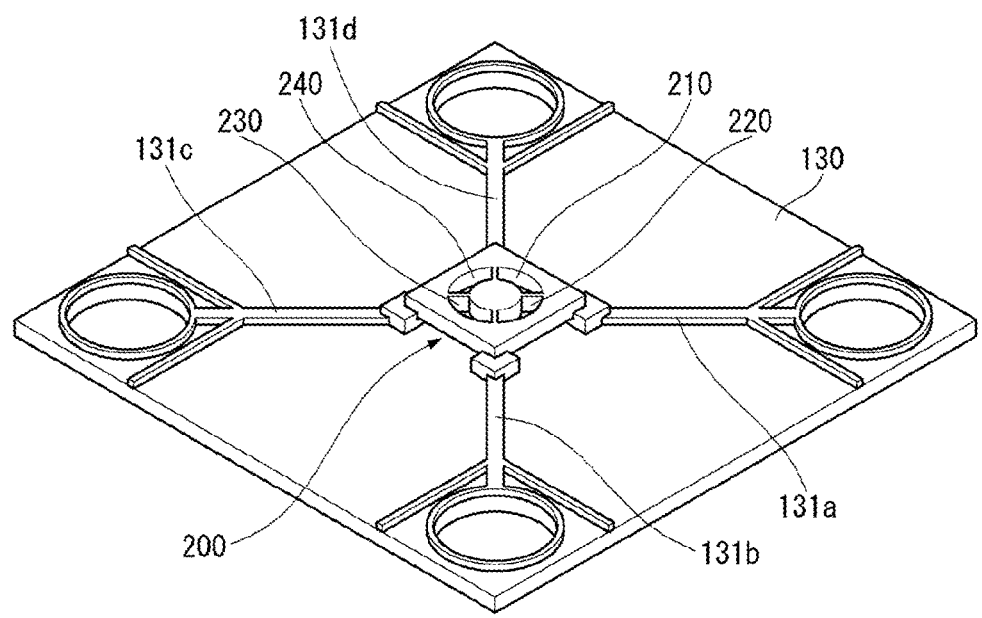

Referring to FIG. 20, the second substrate 200 may be placed on the first substrate 130. In this case, the second substrate 200 may be disposed such that the surface of the second substrate 200 on which the sensing portion 160 (see FIG. 7) is formed faces the surface of the first substrate 130 on which the electrode line 131 of the first substrate 130 are formed.

The second substrate 200 may be placed on the first substrate 130 while being aligned by the bonding pads 134, 135, 136, and 137.

The plurality of openings 210, 220, 230, and 240 may provide outside air to the sensing portion 160 (see FIG. 7). It may mean that the outside air or gas can flow in toward or out from the sensing portion 160 (see FIG. 7) by the plurality of openings 210, 220, 230 and 240 formed on the second substrate 200.

Figure 21:
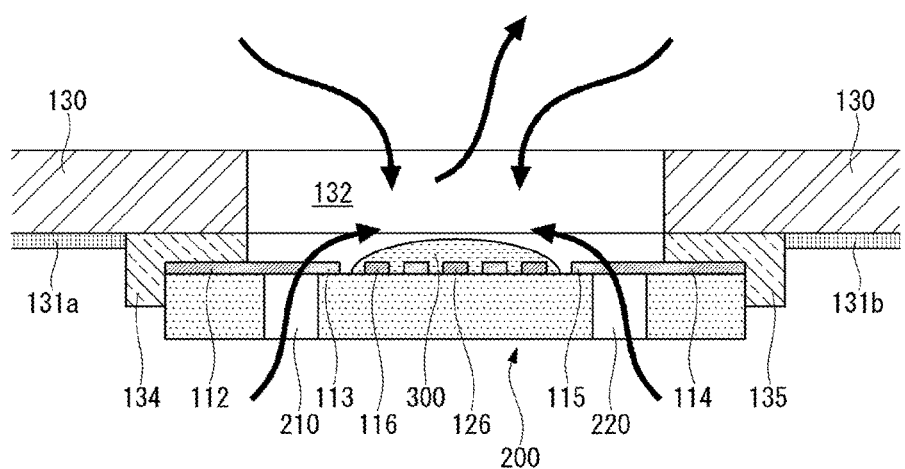

Referring to FIG. 21, the pad electrodes 112 and 114 may be positioned between the first substrate 130 and the second substrate 200. That is, the first substrate 130 may face the second substrate 200 with the pad electrodes 112 and 114 interposed therebetween. The bonding pads 134 and 135 may be positioned between the first substrate 130 and the second substrate 200. That is, the first substrate 130 may face the second substrate 200 with the bonding pads 134 and 135 interposed therebetween.

The pad electrodes 112 and 114 may be positioned between the bonding pads 134 and 135 and the second substrate 200. At this time, the pad electrodes 112 and 114 may be in contact with or bonded to the bonding pads 134 and 135. That is, the pad electrodes 112 and 114 may be bonded to the bonding pads 134 and 135 and electrically connected to each other.

In another point of view, the bonding pads 134 and 135 may be positioned between the pad electrodes 112 and 114 and the first substrate 130. At this time, the bonding pads 134 and 135 may be in contact with or coupled to the pad electrodes 112 and 114. That is, the bonding pads 134 and 135 may be bonded to the pad electrodes 112 and 114 and electrically connected to each other.

In addition, the bonding pads 134 and 135 may partially face the side surface of the second substrate 200. A part of the bonding pads 134 and 135 can guide the overall alignment of the second substrate 200 by limiting the position of the side surface of the second substrate 200.

The side surface of the second substrate 200 may be guided by the bonding pads 134 and 135. That is, the bonding pads 134 and 135 can limit the position of the side surface of the second substrate 200 on the first substrate 130. That is, the second substrate 200 can be aligned in position by the bonding pads 134 and 135.

The heating electrode 116 may be positioned between the first substrate 130 and the second substrate 200. The sensing electrode 126 may also be positioned between the first substrate 130 and the second substrate 200. The sensing portion 300 may also be positioned between the first substrate 130 and the second substrate 200.

The heating electrode 116, the sensing electrode 126 and/or the sensing portion 300 may be disposed adjacent to the opening 132 of the first substrate 130 and may face the opening 132 of the first substrate 130. This structure means that gas can be introduced from the outside through the opening 132 of the first substrate 130 and can contact the sensing portion 300.

In addition, the gas can flow from the outside through the openings 210 and 220 formed in the second substrate 200, and can contact the sensing portion 300. The gas introduced through the openings 132 of the first substrate 130 may be discharged through the openings 210 and 220 of the second substrate 200 or may be discharged through the openings 132 of the first substrate 130. The gas introduced through the openings 210 and 220 of the second substrate 200 may be discharged through the opening 132 of the first substrate 130 or may be discharged through the openings 210 and 220 of the second substrate 200. That is, the fluidity of the gas from the outside to the sensing portion 300 may be improved.

In addition, since a separate housing is not required for protection of the sensing portion 300, it is easy to manufacture the gas sensor. The durability of the gas sensor can be improved by protecting the sensing unit portion by the first substrate 130 and the second substrate 200.

Further, since wire bonding is not required, it is possible to prevent the gas sensor from being lost due to an impact generated during wire bonding.

Figure 22:
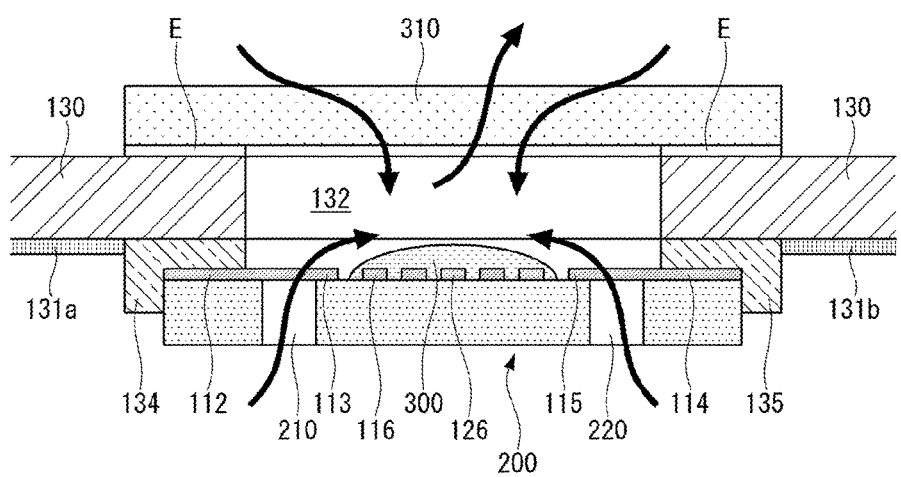

Referring to FIG. 22, the filter 310 may cover the opening 132 of the first substrate 130. The filter 310 may improve the sensitivity of the sensor by removing moisture or the like contained in the gas flowing into or out of the opening 132 of the first substrate 130. The filter 310 may be fixed to the first substrate 130 by an adhesive member E. For example, the adhesive member E may be an epoxy.

If the front surface of the first substrate 130 faces the second substrate 200, the filter 310 may be positioned on the rear surface of the first substrate 130. The filter 310 may be referred to as a first filter 310.

Figure 23:
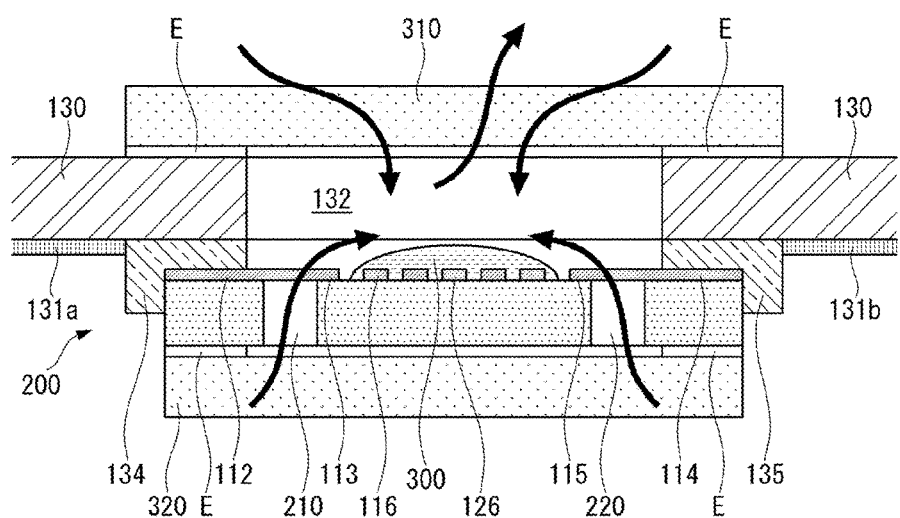

Referring to FIG. 23, the filter 320 may cover the openings 210 and 220 of the second substrate 200. The filter 320 may improve the sensitivity of the sensor by removing moisture or the like contained in the gas flowing into or out of the openings 210 and 220 of the second substrate 200. The filter 320 may be fixed to the second substrate 200 by an adhesive member E. For example, the adhesive member E may be an epoxy.

If the front surface of the second substrate 200 faces the first substrate 130, the filter 320 may be positioned on the rear surface of the second substrate 200. The filter 320 attached to the second substrate 200 may be referred to as a second filter 320.

Figure 24:
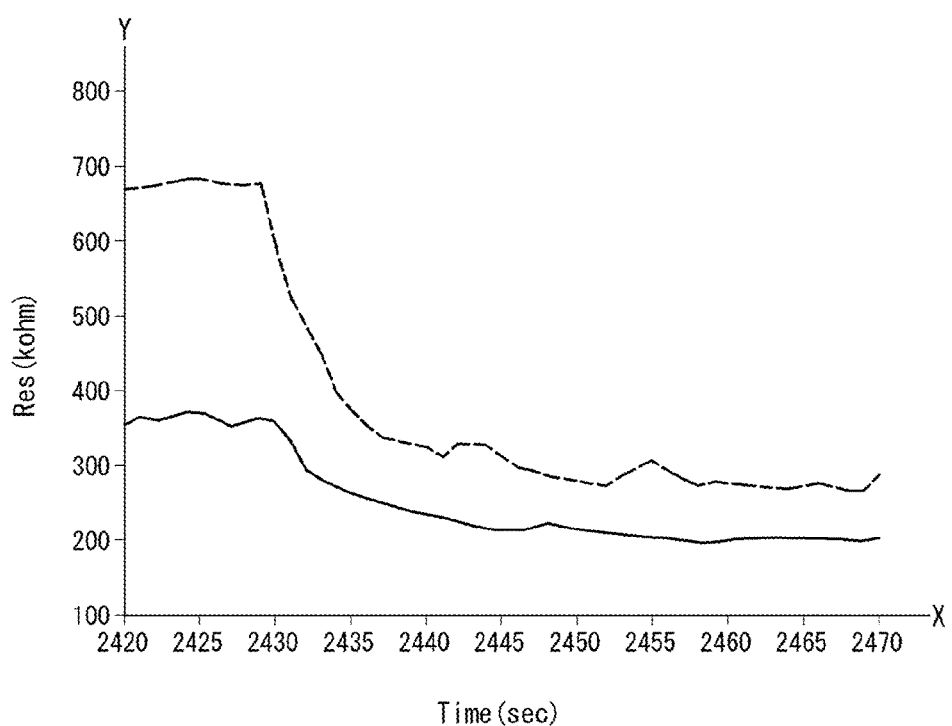
FIG. 24 is a diagram illustrating an example of a sensing effect of a gas sensor according to an embodiment of the present invention.

FIG. 24 is a diagram showing an example of the sensing effect of the gas sensor according to the embodiment of the present invention.

The X axis represents time. The Y axis represents the resistance. The change in resistance value or resistance value is related to the sensitivity of the sensor. The solid line indicates the sensitivity of the conventional gas sensor. The dotted line indicates the sensitivity of the gas sensor according to an embodiment of the present invention.

For example, the heating electrode 116 (see FIG. 23) may heat the sensing portion 300 to about 250 to 300 degrees Celsius. At this time, when approximately 5 ppm of the gas containing ethanol is released, the dotted line has a higher resistance value than the solid line. This means that the sensitivity of the gas sensor is improved.

Certain embodiments or other embodiments of the invention described above are not mutually exclusive or distinct from each other. Any or all elements of the embodiments of the invention described may be combined or combined with each other in configuration or function.

Although embodiments have been described with reference to a number of illustrative embodiments thereof, it should be understood that numerous other modifications and embodiments can be devised by those skilled in the art that will fall within the scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A sensor comprising:
a first substrate;
a second substrate positioned relative to the first substrate;
a first electrode located between the first substrate and the second substrate, the first electrode formed on the second substrate;
a sensing portion covering at least a part of the first electrode and further covering at least a portion of the second substrate;
a pad electrode located between the first substrate and the second substrate, wherein the pad electrode is formed on the second substrate and is electrically coupled to the first electrode;
a bonding pad located between the first substrate and the second substrate, wherein the bonding pad is formed on the first substrate and is electrically coupled to the pad electrode;
an electrode line formed on the first substrate and being electrically coupled to the bonding pad, wherein a height of the bonding pad is greater than a height of the electrode line;
a first filter coupled to the first substrate; and
a second filter coupled to the second substrate;
wherein the first substrate includes a first opening adjacent to the sensing portion, and wherein the first filter is located to cover the first opening,
wherein the second substrate includes a second opening adjacent to the sensing portion, and wherein the second filter is located to cover the second opening, and
wherein the bonding pad partially faces a side surface of the second substrate.

2. The sensor of claim 1, wherein positioning of the first opening relative to the second opening permits gas exchange in and out of the sensor through the first opening and the second opening.

3. The sensor of claim 1, wherein
the second substrate includes:
an outer substrate including an hollow space located at a central portion of the outer substrate;
an inner substrate located in the hollow space, the inner substrate spaced apart from the outer substrate; and
a bridge electrically coupling the outer substrate with the inner substrate.

4. The sensor of claim 3, wherein the pad electrode is positioned on the outer substrate, wherein the first electrode is positioned on the inner substrate, and wherein the first electrode is electrically coupled with the pad electrode via the bridge.

5. The sensor of claim 1, wherein the bonding pad includes a guide, and wherein the guide faces the side surface of the second substrate.

6. The sensor of claim 1, wherein the first electrode includes:
a heating electrode electrically insulated from the sensing portion; and
a sensing electrode electrically coupled to the sensing portion.

7. The sensor of claim 6, wherein the sensing electrode is positioned in a layer, and wherein the heating electrode is positioned in another layer.

8. The sensor of claim 6, wherein the sensing electrode is positioned in a layer in which the heating electrode is positioned.

9. The sensor of claim 1, wherein the bonding pad forms a stepped portion, and wherein a corner of the second substrate is positioned adjacent to the stepped portion.

10. The sensor of claim 1, wherein the sensing portion includes a metal oxide.

11. The sensor of claim 1, wherein the sensing portion is formed on the second substrate.

12. The sensor of claim 1, wherein the first substrate includes an opening that is located to cooperate with the sensing portion.

13. The sensor of claim 1, wherein the first substrate includes an opening that is aligned relative to the sensing portion.

14. The sensor of claim 1, wherein a top side of the second substrate faces a bottom side of the first substrate.

* * * * *